US006582426B2

(12) United States Patent
Moorman et al.

(10) Patent No.: US 6,582,426 B2
(45) Date of Patent: Jun. 24, 2003

(54) NEEDLE KIT AND METHOD FOR MICROWAVE ABLATION, TRACK COAGULATION, AND BIOPSY

(75) Inventors: Jack W. Moorman, Los Gatos, CA (US); M. Elizabeth Bush, Fremont, CA (US)

(73) Assignee: Vivant Medical, Inc., Mountain View, CA (US)

( * ) Notice: Subject to any disclaimer, the term of this patent is extended or adjusted under 35 U.S.C. 154(b) by 89 days.

(21) Appl. No.: 09/827,528

(22) Filed: Apr. 6, 2001

(65) Prior Publication Data

US 2001/0039416 A1 Nov. 8, 2001

Related U.S. Application Data

(63) Continuation of application No. 09/356,077, filed on Jul. 16, 1999, now Pat. No. 6,355,033, which is a continuation-in-part of application No. 09/336,371, filed on Jun. 17, 1999, now Pat. No. 6,306,132.

(51) Int. Cl.[7] .............................................. A61B 18/18
(52) U.S. Cl. ........................ 606/33; 606/41; 600/562; 607/101
(58) Field of Search ............................ 606/33, 34, 35, 606/41; 607/100, 101; 604/19–22; 600/562–572

(56) References Cited

U.S. PATENT DOCUMENTS

| 3,598,108 | A | 8/1971 | Jamshidi et al. |
| 3,886,944 | A | 6/1975 | Jamshidi |
| 4,448,198 | A | 5/1984 | Turner |

(List continued on next page.)

FOREIGN PATENT DOCUMENTS

| WO | WO 98/06341 | 2/1998 |
| WO | WO 00/56239 | 9/2000 |

OTHER PUBLICATIONS

Andriole, J.G. et al., (1983). "Biopsy Needle Characteristics Assessed in the Laboratory," *Radiology* 148:659–662.

Durney, C.H. et al., (1988) "Antennas for Medical Applications," In *Antenna Handbook: Theory Application and Design*, Lo, V.T. and Lee, S.W. (Eds.) Van Nostrand Reinhold: New York, pp. 24–40.

Gottlieb, C.F. et al. (1990). "Interstitial Microwave Hyperthermia Applicators having Submillimetre Diameters," *Int. J. Hyperthermia* 6(3):707–714.

Iskander, M.F. et al., (1989). "Design Optimization of Interstitial Antennas," *IEEE Transactions on Biomedical Engineering* 36(2):238–246.

Labonte, S. et al., (1995). "Monopole Antennas for Microwave Catheter Ablation," *IEEE Trans. on Microwave Theory and Techniques* 44(10):1832–1840.

Matsukawa, T. et al. (1997). "Percutaneous Microwave Coagulation Therapy in Liver Tumors," *Acta Radiologica* 38:410–415.

(List continued on next page.)

*Primary Examiner*—Rosiland S. Kearney
(74) *Attorney, Agent, or Firm*—Morrison & Foerster LLP

(57) ABSTRACT

A modular biopsy, ablation and track coagulation needle apparatus is disclosed that allows the biopsy needle to be inserted into the delivery needle and removed when not needed, and that allows an inner ablation needle to be introduced and coaxially engaged with the delivery needle to more effectively biopsy a tumor, ablate it and coagulate the track through ablation while reducing blood loss and track seeding. The ablation needle and biopsy needle are adapted to in situ assembly with the delivery needle. In a preferred embodiment, the ablation needle, when engaged with the delivery needle forms a coaxial connector adapted to electrically couple to an ablating source. Methods for biopsying and ablating tumors using the device and coagulating the track upon device removal are also provided.

57 Claims, 7 Drawing Sheets

U.S. PATENT DOCUMENTS

| | | |
|---|---|---|
| 4,565,200 A | 1/1986 | Cosman |
| 4,825,880 A | 5/1989 | Stauffer et al. |
| 5,085,659 A | 2/1992 | Rydell |
| 5,171,255 A | 12/1992 | Rydell |
| 5,370,675 A | 12/1994 | Edwards et al. |
| 5,405,346 A | 4/1995 | Grundy et al. |
| 5,470,308 A | 11/1995 | Edwards et al. |
| 5,507,743 A | 4/1996 | Edwards et al. |
| 5,578,030 A | 11/1996 | Levin |
| 5,599,295 A | 2/1997 | Rosen et al. |
| 5,607,389 A | 3/1997 | Edwards et al. |
| 5,683,384 A | 11/1997 | Gough et al. |
| 5,853,366 A | 12/1998 | Dowlatshahi |
| 5,861,002 A | 1/1999 | Desai |
| 6,106,524 A | 8/2000 | Eggers et al. |
| 6,146,378 A | 11/2000 | Mikus et al. |
| 6,162,216 A | 12/2000 | Guziak et al. |
| 6,178,354 B1 | 1/2001 | Gibson |
| 6,325,796 B1 * | 12/2001 | Berube et al. ............. 606/33 |

OTHER PUBLICATIONS

Murakami, R. et al., (1995). "Treatment of Hepatocellular Carcinoma: Value of Percutaneous Microwave Coagulation," *American Journal of Radiology* (*AJR*) 164:1159–1164.

Seki, T. et al., (1994). "Ultrasonically Guided Percutaneous Microwave Coagulation Therapy for Small Hepatocellular Carcinoma," *Cancer* 74(3): 817–825.

Stauffer, P.R. et al., "Interstitial Heating Technologies," In *Thermoradiotherapy and Thermochemotherapy vol. 1: Biology, Physiology, Physics*, Seegenschniedt, M.H. et al. (Eds.), Berlin: Springer pp. 279–320.

\* cited by examiner

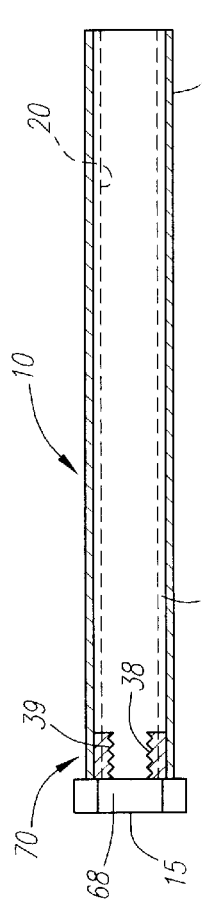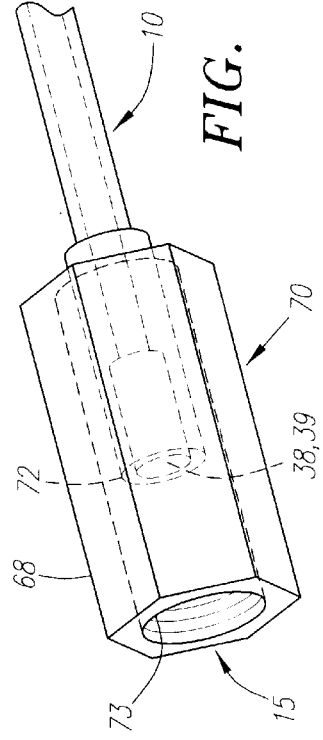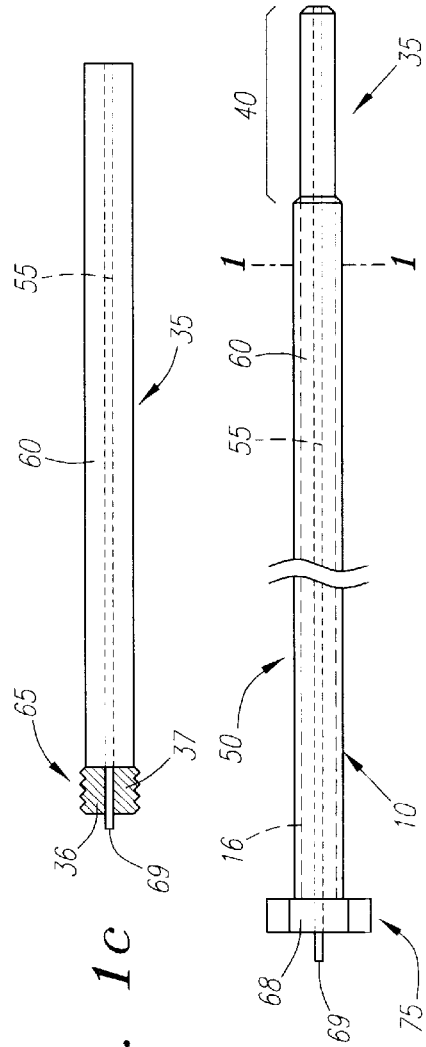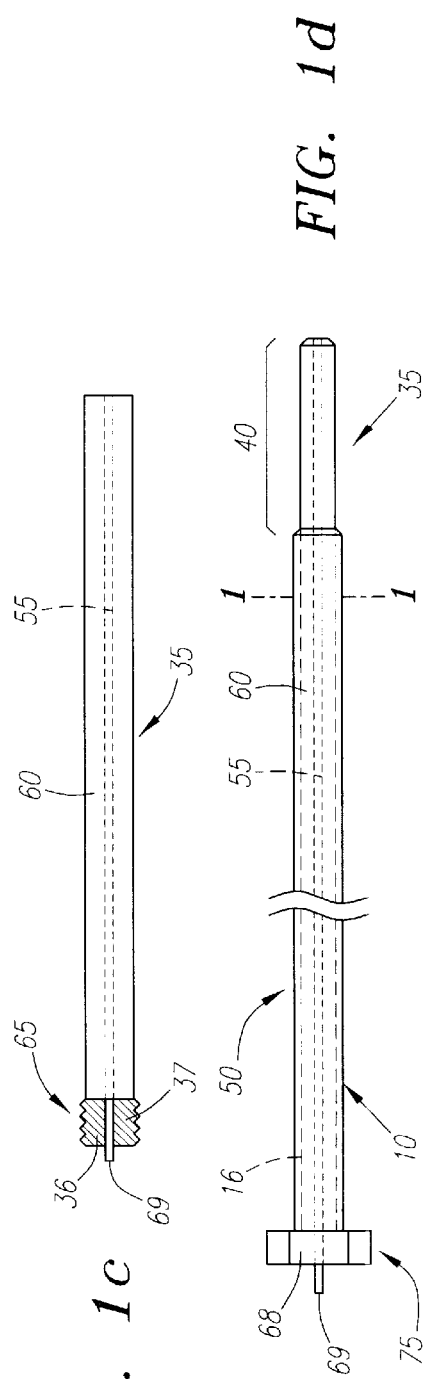

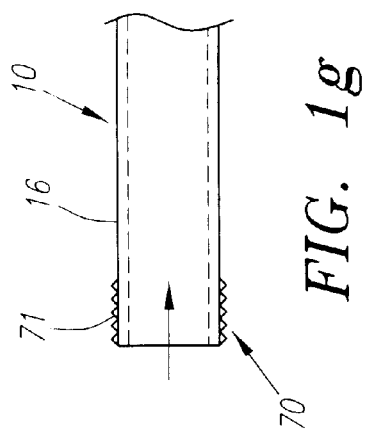
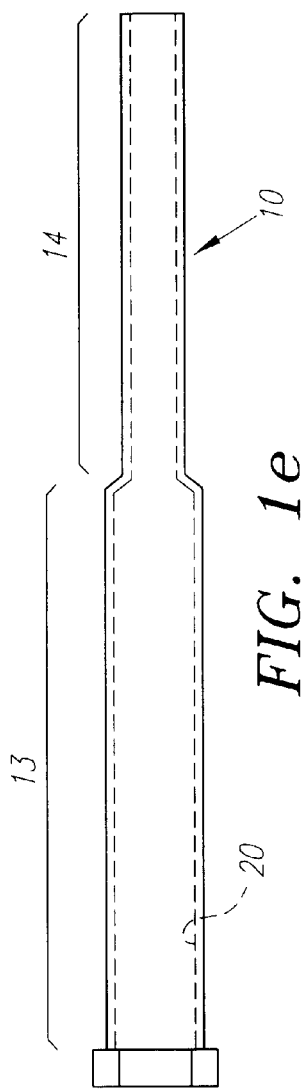
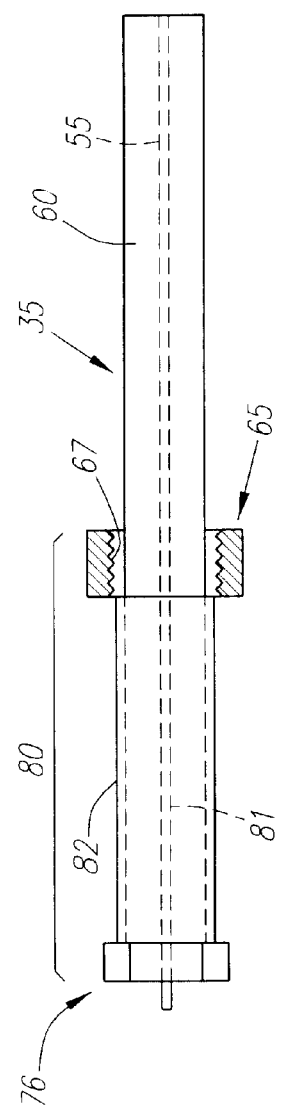

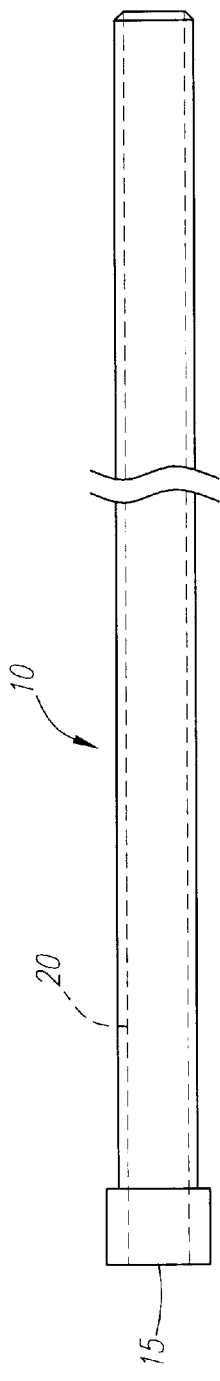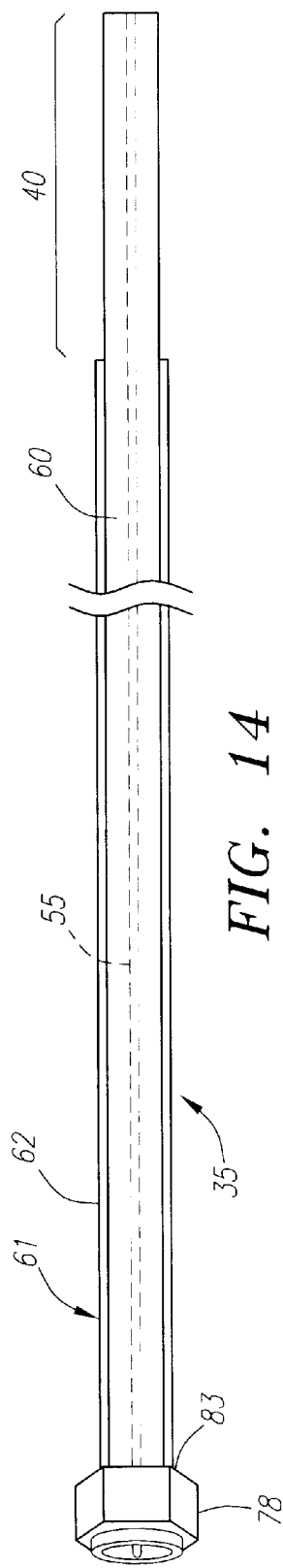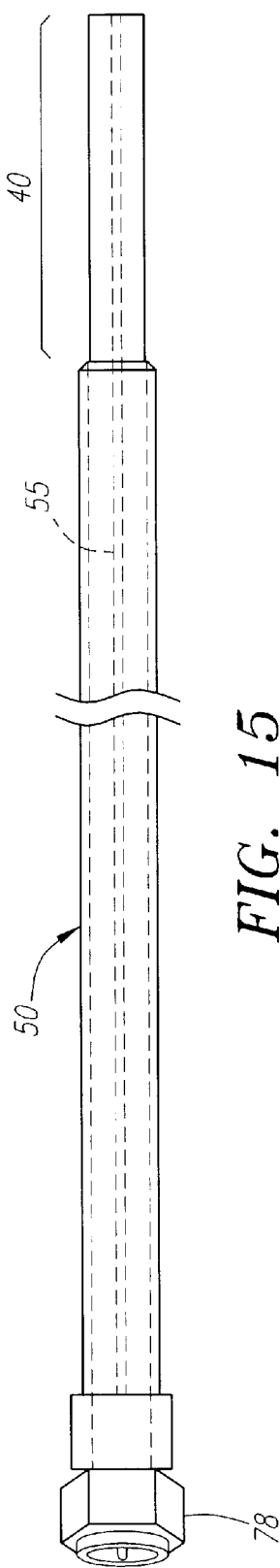

NEEDLE KIT AND METHOD FOR MICROWAVE ABLATION, TRACK COAGULATION, AND BIOPSY

RELATED APPLICATION

This application is a Continuation of application Ser. No. 09/356,077, filed Jul. 16, 1999 now U.S. Pat. No. 6,355,033 hereby incorporated in full by reference, which is a continuation-in-part of application Ser. No. 09/336,371, filed Jun. 17, 1999 now U.S. Pat. No. 6,306,132.

This application is related to U.S. application "Modular Biopsy and Microwave Ablation Needle Delivery Apparatus Adapted to In Situ Assembly and Method of Use" filed on Jun. 17, 1999, the contents of which are incorporated by reference.

FIELD OF THE INVENTION

The present invention relates generally to a modular biopsy, ablation and delivery needle apparatus that allows a biopsy needle to be inserted into a delivery needle, and, absent the biopsy needle, allows an inner ablation needle to be introduced and engaged with the delivery needle to form a microwave antenna. The present invention also relates to methods for biopsying and ablating tumors and coagulating the insertion track using the modular apparatus.

BACKGROUND OF THE INVENTION

In the U.S., the lifetime chance of developing an invasive cancer is 46% for men and 38% for women. Cancer is the second leading cause of death in the U.S. and is a major cause of death worldwide. In the U.S. in 1998, there were an estimated 564,800 deaths due to cancer with 1,228,600 new cases of invasive cancer diagnosed. Over 40% of the deaths are associated with primary and metastatic liver cancer.

Outside the U.S., primary liver cancer (hepatocellular carcinoma) accounts for one of the largest cancer-related mortalities in the world (about 1,250,000 per year) in adults. In Japan, liver cancer is the third most common cause of death in men.

Of the over 1 million newly diagnosed U.S. cancer patients each year, hundreds of thousands will develop liver cancer during the course of the disease. For liver metastases that result in or are associated with death, estimates vary but are conservatively estimated at more than 230,000 annually in the U.S. Numerous studies of colorectal carcinoma have shown that liver metastasis is the primary determinant of patient survival.

Patterns of metastasis can be explained in part by the architecture of the circulatory system. Cancers in the intestine and many other tissues often colonize the liver first because the liver contains the first downstream capillary bed. It is estimated that 131,600 new cases of colorectal cancer were detected in 1998 and that 98,000 of them will eventually have liver involvement. Due to a lack of treatment options and the likelihood of recurrence, the American Joint Committee on Cancer projects that less than 1% of the patients diagnosed with nonresectable liver metastasis will be alive in 5 years.

Unfortunately, except for the small number of patients who have a form of cancer that can be surgically resected, there is no effective treatment. Therapies for nonresectable tumors include chemotherapy, radiation, transcatheter arterial embolization, chemoembolization and cryotherapy. Of particular interest are the percutaneous ablative techniques using ethanol, acetic acid, hot saline solution, laser, radiofrequency (RF), microwave, gene therapy and focused ultrasound.

Recent improvements in computed tomography (CT), ultrasound imaging and magnetic resonance imaging (MRI) have enabled physicians to detect tumors at an earlier stage and to locate them more precisely. These improvements have increased the use of laparoscopic and percutaneous procedures. As a result, RF, microwave, and cyroprobe devices have been developed to be used in the treatment of preselected sites. A number of problems exist with respect to these currently available devices. For example, cyroprobes generally require laparotomy because of their relatively large diameter, precluding a simpler, less traumatic approach. RF ablation relies on electrical conduction to deliver energy to tissues away from an RF ablation electrode. As tissue adjacent to the RF ablation electrode becomes desiccated or charred, the impedance increases, thereby limiting conduction through the desiccated or charred tissue. In addition, scar tissue, blood vessels or other tissue inhomogeneity within the ablation site may alter the conduction path of the RF current. Microwave coagulation therapy (MCT), however, destroys the diseased tissue though propagation of electromagnetic waves from a microwave antenna. Because the energy is deposited into the tissue away from the antenna without relying solely on conduction currents, little or no charring occurs with microwave coagulation therapy as compared to RF ablation methods. Furthermore, any charring that might occur does not affect energy deposition patterns to the extent that it would for RF ablation methods because energy can be propagated beyond any charred tissue since conduction through the charred tissue is not required. Therefore, microwave antennas can ablate tissue with little or no charring and with little or no alteration of their energy deposition patterns (typically measured by a specific absorption rate (SAR)) by tissue inhomogeneities. Despite the advantages offered by MCT, a need in the art exists for small-diameter microwave antennas that can precisely follow the biopsy needle track.

This need in the art is particularly acute in liver surgery. For instance, excessive bleeding and bile leakage during surgical procedures within the liver are common. Not surprisingly, large instruments are more traumatic than smaller ones. Furthermore, attempts at biopsy and thermotherapy of tumors can result in seeding of the carcinoma along the track during instrument removal and additional bleeding along the track. Localizing the tumor site can also be a problem and can result in additional trauma and bleeding, for instance, when a biopsy tool is used to sample and localize the tumor and subsequently the thermotherapy device is reinserted to treat the tumor.

Accordingly, there is a need for a small diameter delivery device that can facilitate the biopsy and ablation of a tumor through a single protected puncture site without the need to withdraw the device from the puncture site during biopsying and ablation. Further, there is a need for a device that can efficiently ablate the track during removal to reduce bleeding and the chances of track seeding.

SUMMARY OF THE INVENTION

The present invention is directed to a modular biopsy and microwave ablation needle and delivery apparatus adapted for in situ assembly, biopsy and ablation of tumors in tissues, and ablation of the track upon removal of the apparatus. More particularly the apparatus is adapted to the biopsy and ablation of tumors in solid organs that have a propensity to bleed, for instance, the liver. The present invention also relates to methods for the biopsy and ablation of tumors using the modular biopsy and microwave ablation needle and delivery apparatus.

Generally, a modular needle apparatus for performing biopsy and ablation of tissue abnormalities through a puncture site comprises an elongated hollow delivery needle, a biopsy needle, and an ablation needle. The hollow delivery needle extends longitudinally a first predetermined distance from an open proximal end to an open distal end, with a lumen extending therebetween. The lumen may accommodate either the biopsy needle or the ablation needle inserted through the open proximal end. The distal end of the delivery needle may be sharpened to pierce tissue. Alternatively or additionally, an obturator may be inserted within the lumen of the delivery needle to stiffen the delivery needle and provide a sharp tip to facilitate piercing tissue. As yet another alternative, the biopsy needle acts as the obturator of the delivery needle, and the biopsy needle and delivery needle are inserted into tissue as a unit. In that case, the biopsy needle itself serves to stiffen the assembly and provide a sharp point for piercing tissue. The biopsy needle may be of any type known in the art and may comprise a single piece, two pieces, or more.

Both the biopsy needle and the ablation needle are longer than the first predetermined distance such that when either the biopsy needle or the ablation needle is inserted into the proximal port and distally displaced within the lumen of the delivery needle, a distal projection of either the biopsy needle or the ablation needle may extend beyond the distal end of the delivery needle. The distal projection of the ablation needle is adapted to form a microwave antenna. The microwave antenna may comprise one of many forms known in the art, for example, a monopole, a dipole or a helical coil antenna.

In a preferred embodiment, the delivery needle has a first connector adapted to connect to a second connector of the ablation needle when the ablation needle is inserted within the lumen of delivery needle. The ablation needle comprises a center conductor at least partially surrounded by a dielectric material, and the delivery needle comprises a conducting material wherein the combination of the delivery needle, the dielectric material and the center conductor comprise a coaxial transmission line when the first and second connectors are connected. The delivery needle thus comprises the outer conductor of the coaxial transmission line and the inner conductor of the ablation needle comprises the inner conductor of the coaxial transmission line. The ablation needle extends longitudinally a second predetermined distance from the second connector wherein the second predetermined distance is greater than the first predetermined distance whereby the ablation needle forms the distal projection extending beyond the distal end of the delivery needle when the first and second connectors are connected. The distal projection of the ablation needle forms the microwave antenna that is coupled to the coaxial transmission line.

In another embodiment of the invention, the delivery needle and the ablation needle are not adapted to form a transmission line. Instead, the transmission line is contained within the ablation needle. The delivery needle extends longitudinally a first predetermined distance from an open proximal end to an open distal end, with a lumen extending therebetween as described generally above. The ablation needle extends longitudinally a third predetermined distance from a distal end wherein the third predetermined distance is greater than the first predetermined distance whereby the ablation needle forms a distal projection extending beyond the distal end of the delivery needle when the ablation needle is distally displaced within the lumen of the delivery needle. The distal projection of the ablation needle forms the microwave antenna. The remainder of the ablation needle comprises a transmission line that couples to the microwave antenna. The microwave antenna may be a dipole, a monopole or a helical coil antenna.

For the embodiments described herein, the biopsy needle, which may be an aspirating or a coring type, extends distally from its proximal end a fourth predetermined distance wherein the fourth predetermined distance is greater than the first predetermined distance. The biopsy needle may comprise a cannula and a stylet adapted to be disposed within the cannula. The stylet may include a matched point wherein the matched point matches a distal end of the cannula.

Methods of ablating tissue are also described. First, an ablation system as described herein is provided. Then, the distal end of the delivery needle is introduced into a tissue sample in a predetermined area. Next, the distal end of the ablating needle is inserted into the lumen of the delivery needle through the open proximal end, and the ablating needle is then advanced until the first and second connectors are adjacent one another. Next, the first and second connectors are connected. Then, a coaxial connector of the modular needle apparatus is electrically coupled to a coaxial connector of the microwave energy source. Microwave energy may then be delivered to the microwave antenna, thus ablating the tissue abnormality in the predetermined area. In other embodiments, the steps of inserting a biopsy needle into the delivery needle, biopsying the tissue and removing the biopsy needle with a tissue sample precede or follow the step of inserting the ablation needle.

Withdrawing the ablation needle from the tissue sample after the ablation of the tissue abnormality has been performed leaves an insertion track. The ablation needle may "seed" diseased cells within the insertion track as the ablation needle is withdrawn. The present invention is directed towards devices and methods to ablate the insertion track, thereby killing any diseased cells within the insertion track. In addition, track ablation minimizes bleeding, and, if performed within the liver, stems bile leakage. To minimize the damage to healthy tissue, the insertion track should be ablated with minimal overlap between adjacent ablations. Thus, the modular needle apparatus preferably has a plurality of first markings on its surface wherein the plurality of first markings are spaced apart a distance approximately equal to an effective antenna length of the microwave antenna. After ablating the tissue abnormality, a clinician may partially withdraw the ablation needle from the insertion track approximately an effective antenna length as gauged by observing the plurality of first markings. The clinician may then perform an ablation of the insertion track. The steps of partially withdrawing and ablating the insertion track may be repeated as required to complete the track ablation. To aid the determination of whether the track ablation has been completed, the modular needle apparatus preferably further comprises a second marking adjacent a proximal edge of an antenna radiation pattern of the microwave antenna. In such an embodiment, the steps of partially withdrawing the modular needle apparatus and ablating the insertion track are repeated until a partial withdrawing of the modular needle apparatus positions the second marking adjacent an edge of an organ containing the tissue abnormality. At this point, the partial withdrawing step is stopped and a final ablation of the insertion track performed. Note that although the plurality of first markings and the second markings are described with respect to the delivery needle of the present invention, these markings may be applied to any suitable interstitial ablation device.

Because only a small area surrounding the insertion track need be ablated to prevent seeding, bleeding and (if applicable) bile leakage, the clinician may decrease the diameter of the field of the antenna and/or lengthen the field to speed track ablation time. Such changes in the field will also minimize damage to healthy tissue surrounding the insertion track.

It is to be noted that the plurality of first markings and the second marking and methods of using the same may be applied to other interstitial thermotherapy devices such as RF ablation devices or cryoprobes. In these embodiments, the plurality of first markings would be spaced apart an "effective ablation" length which is defined analogously to the effective antenna length. The effective ablation length thus represents the extent of effectively ablated tissue after performing an ablation with the interstitial thermotherapy device.

Additional objects and features of the present invention will become apparent from consideration of the following description taken in conjunction with the accompanying drawings.

BRIEF DESCRIPTION OF THE DRAWINGS

FIG. 1a is a side view of a hollow delivery needle wherein the first connector comprises an outer portion of a coaxial connector according to one embodiment of the invention.

FIG. 1b is an isometric view of the proximal end of the hollow delivery needle of FIG. 1a.

FIG. 1c is a side view of an ablation needle wherein the second connector comprises an inner portion of a coaxial connector according to one embodiment of the invention.

FIG. 1d is a side view of a modular needle apparatus wherein the ablation needle of FIG. 1b is connected to the delivery needle of FIG. 1a.

FIG. 1e is a side view of the delivery needle wherein a distal portion is narrower in diameter than the remainder of the delivery needle.

FIG. 1f is a side view of an ablation needle further comprising a proximal coaxial extension wherein the second connector comprises a threaded portion at the distal end of an outer conductor of the proximal coaxial extension.

FIG. 1g is a side view of a delivery needle wherein the first connector comprises a threaded portion at its proximal end.

FIG. 13 is a side view of the delivery needle not adapted to form a coaxial transmission line in combination with the ablation needle according to one embodiment of the invention.

FIG. 14 is a side view of the ablation needle not adapted to form a coaxial transmission line in combination with the delivery needle according to one embodiment of the invention.

FIG. 15 is a side view of a modular needle apparatus wherein the ablation needle of FIG. 14 is inserted within the lumen of the delivery needle of FIG. 13 according to one embodiment of the invention.

DETAILED DESCRIPTION OF THE PREFERRED EMBODIMENTS

Figure 2:
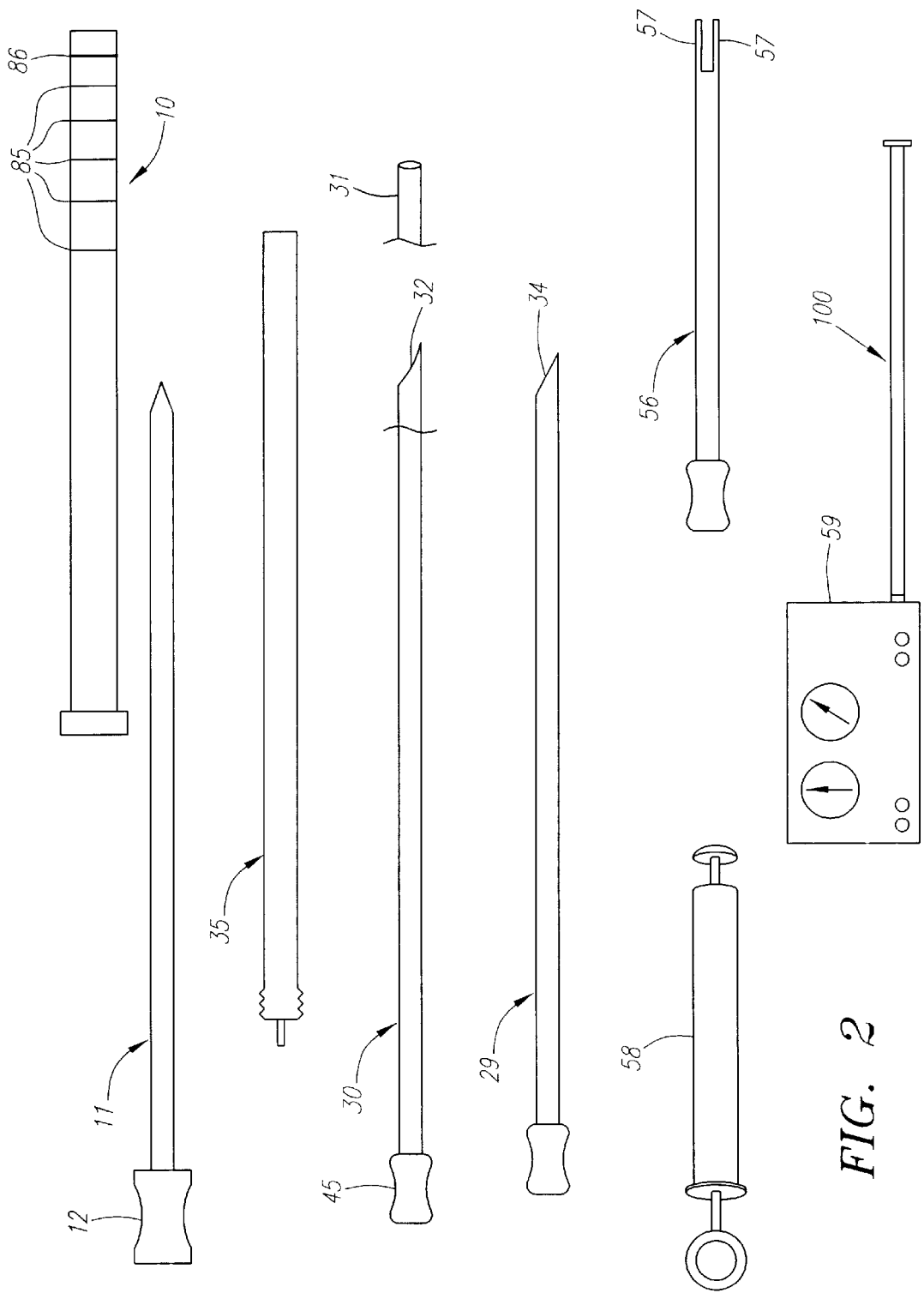
FIG. 2 is a side view of a tissue biopysing and ablating system including the hollow delivery needle of FIG. 1a and the ablation needle of FIG. 1c.

Turning now to FIGS. 1a through 2 and 13 through 15, various embodiments of the modular needle apparatus are illustrated. In each of these embodiments, the modular needle apparatus includes a hollow delivery needle 10 having a proximal port 15 opening into a lumen 20 which extends through the delivery needle 10 to its distal end. The lumen 20 is sized to accommodate alternately a biopsy needle 30 and an ablation needle 35. Both the biopsy needle 30 and the ablation needle 35 are longer than the delivery needle 10 such that when either is inserted into the proximal port 15, a distal projection may extend from the distal end of the delivery needle 10. In this fashion, the biopsy needle 30 may obtain a tissue sample. In addition, the distal projection of the ablation needle 35 forms a microwave antenna 40 for performing tissue ablation. In certain embodiments, illustrated in FIGS. 1a through 1g, inserting the ablation needle 35 into the lumen 20 of the delivery needle 10 forms a coaxial transmission line 50 which supplies power to the microwave antenna 40. In such embodiments, the delivery needle 10 comprises a conductive material that functions as the outer conductor 16 of the coaxial transmission line 50, while a center conductor 55 of the ablation needle 35 circumferentially surrounded by dielectric material 60 acts as the center conductor and dielectric of the coaxial transmission line 50. Delivery needle 10 preferably further comprises a jacket 17 of electrically and/or thermally insulating material such as parylene or Teflon® which at least partially surrounds outer conductor 16 (shown in FIG. 1a). Delivery needle 10 may have a flat or a sharpened distal end. As used herein, a "flat" distal end indicates a bevel of 90° as described in Andriole et al., Biopsy Needle Characteristics Assessed in the Laboratory, *Radiology* 148: 659–662, September 1983, the contents of which are hereby incorporated by reference.

In an alternate embodiment, illustrated in FIGS. 13 through 15, the microwave antenna 40 couples to a transmission line 61 contained entirely within the ablation needle 35 such that the delivery needle 10 has no electrical transmission function, although it may provide additional shielding and/or act as an insulator. Thus, in these embodiments, the delivery needle 10 and the ablation needle 35 do not couple together to create the coaxial transmission line 50 of FIG. 1*d*.

It is to be noted that by coupling the delivery needle 10 with the ablation needle 35 to create the coaxial transmission line 50 feeding the microwave antenna 40, the largest diameter that must enter the tissue may be kept very small, preferably of 17 gauge or higher, and more preferably 18 gauge or higher. As used herein, "gauge" shall refer to the outer diameter of a needle unless otherwise indicated. For such embodiments, the ablation needle 35 comprises a center conductor 55 circumferentially surrounded by a dielectric material 60. The dielectric material 60 may comprise a ceramic material, a fluoropolymer such as polytetrafluoroethylene (PTFE) or expanded PTFE, polyethylene (PE), silicone or other suitable materials. The dielectric material 60 is sized to fill the lumen 20 of the delivery needle 35. The diameter of the center conductor 55 and the inner diameter of the outer conductor 16 are chosen according to the equation:

$$Z = (138/(\epsilon)^{1/2}) \log_{10}(D/d)$$

where Z is the characteristic impedance, 6 is the dielectric constant of the dielectric material 60, D is the inner diameter of outer conductor 16, and d is the diameter of center conductor 55. Typically, Z is chosen to be 50 Ω. The value of $\epsilon$ is typically between 1 and 10, for example, the s of PTFE is 2.1.

In addition, to promote efficient conduction along the coaxial transmission line 50, the inner surface of outer conductor 16 of the delivery needle 10 may be coated with a layer of very conductive metal such as Ag, Au, Cu or Al preferably to a thickness of at least the skin depth, or depth of penetration, δ. The skin depth in meters is given by the following equation:

$$\delta = \mathrm{Sqrt}(2/((\omega\,\mu\,\sigma))$$

where ω=2 π frequency (in Hz), $\mu$ is the permeability (or rate of absorption) of the very conductive metal in henrys/meter, and σ is the conductance in mhos/meter. Similarly, the base metal forming the center conductor 55 in the ablation needle 35 may be coated with a layer of a very conductive metal preferably to a thickness of at least the skin depth.

To complete the coaxial transmission line 50, the ablation needle 35 and the delivery needle 10 are coupled together using a first connector 70 on the delivery needle 10 and a second connector 65 on the ablation needle 35. The first and second connectors 70 and 65 may be implemented in many different ways. For example, in a preferred embodiment, illustrated in FIGS. 1*a* through 1*c*, the first connector 70 on the delivery needle 10 comprises an outer contact 72 for a coaxial connector 75 at the proximal end of the delivery needle 10. Similarly, the second connector 65 on the ablation needle 35 comprises an inner contact 69 for coaxial connector 75 at the proximal end of the ablation needle 35. The second connector 65 on the ablation needle 35 further comprises a connector dielectric material 36 surrounding a portion of inner contact 69. Additional connector dielectric material 39 may optionally line a portion of the lumen of outer contact 72. First and second connectors 70 and 65 are adapted to connect together to form a coaxial connector 75 after the ablation needle 35 is inserted in the proximal port 15 of the delivery needle and distally displaced to bring the connectors 65 and 70 into contact. The adaptations on the connectors 65 and 70 may comprise a number of embodiments. For example, as shown, external threads 37 may be provided in the connector dielectric material 36 and internal threads 38 may be provided in the connector 70 to allow second connector 65 to threadably engage first connector 70. In such an embodiment, a suitable assembly tool 56 for use in threadably engaging connectors 65 and 70 is illustrated in FIG. 2. The assembly tool 56 includes tabs 57 for engaging slots (not illustrated) in the dielectric material 36 of the second connector 65. To complete assembly, a clinician would distally displace the ablation needle 35 within the lumen 20 of the delivery needle 10 until the threads 37 and 38 contact each other. The clinician would then insert the tabs 57 of the assembly tool 56 into the slots of the dielectric material 36 and rotate the assembly tool 56 to threadably engage threads 37 and 38, completing the formation of the coaxial connector 75.

Those of ordinary skill in the art will appreciate the numerous ways in which connectors 65 and 70 may engage one another to form coaxial connector 75. For example, rather than using threads 37 and 38, a latching mechanism using biased tabs engaging matching grooves may be employed. Regardless of the manner in which connectors 65 and 70 connect together, the result is that the inner contact 69 of the coaxial connector 75 electrically couples to the center conductor 55 of the ablation needle 35. Similarly, the outer contact 72 electrically couples to the outer conductor 16 of delivery needle 10. As used herein, "electrically coupled" shall indicate a coupling capable of conducting current at microwave frequencies. In this fashion, a microwave power source (not illustrated) coupled to the coaxial connector 75 will transmit energy through the coaxial transmission line 50 to the microwave antenna 40. First connector 70, and therefore coaxial connector 75, further comprises a nut 68 having internal threads 73 or other mechanical means for insuring firm connection between the coaxial connector 75 and a flexible coaxial cable coupled to the microwave power source. Nut 68 freely rotates about delivery needle 10.

In an alternative embodiment, first and second connectors 70 and 65, illustrated in FIGS. 1*f* and 1*g*, the ablation needle 35 further comprises a proximal coaxial extension 80. A center conductor 81 of the coaxial extension 80 is electrically coupled to the center conductor 55 in the ablation needle 35. The coaxial extension 80 includes an outer conductor 82 that ends distally in the second connector 65. The coaxial extension 80 ends proximally in coaxial connector 76. The delivery needle 10 ends proximally in the first connector 70 such that when the first and second connectors 70 and 65 and connected, the outer conductor 82 of the coaxial extension 80 is electrically coupled to the outer conductor 16 of the delivery needle 10. In this fashion, microwave energy coupled to the coaxial connector 76 electrically couples to the coaxial transmission line 50 through the coaxial extension 80. The first connector 70 may comprise threads 71 on the outer surface of the outer conductor 16. Similarly, the second connector may comprise threads 67 on the inner surface of the outer conductor 82 wherein threads 71 and 67 are adapted to threadably engage one another. Those of ordinary skill in the art will appreciate that alternate means such as the biased tabs and matching grooves previously described may be used instead of threads 71 and 67.

Regardless of whether the ablation needle 35 and the delivery needle couple together to create the coaxial transmission line 50, to minimize trauma and bleeding, particularly in organs like the liver that tend to bleed, the delivery needle 10 is preferably 17 gauge or higher. However, as illustrated in FIG. 1*e*, although the delivery needle 10 may have a distal portion 14 that is 17 gauge or higher, a proximal portion 13 of the delivery needle 10 may be thicker in diameter, for example, 12 gauge or less. Only the distal portion 14 would penetrate sensitive tissue such as the liver; the proximal portion 13 may either not penetrate the body at all (as in an open surgical procedure) or may penetrate only skin and muscle such as during a percutaneous procedure. The added diameter in the proximal portion 13 allows the proximal portion of the coaxial transmission line 50 to have a larger diameter and therefore be less lossy. The larger diameter also helps to improve rigidity in the proximal portion 13. Furthermore, in some embodiments such as those of FIGS. 13–15, it allows greater maneuverability of the biopsy and ablation needles through delivery needle 10. It is to be noted that as the outer diameter of delivery needle 10 changes from that in proximal portion 13 to the diameter of distal portion 14, the diameter of lumen 20 also may change accordingly. In addition, the outer diameter of the dielectric material 60 of ablation needle 35 would change accordingly to create the coaxial transmission line 50.

Turning now to FIG. 2, the hollow delivery needle 10 may include an obturator 11 adapted to be slidably disposed within the lumen 20. The obturator 11 includes a proximal handle 12. With the obturator 11 inserted in the lumen 20 through the proximal port 15, the handle 12 acts as a stop, engaging the proximal port 15 on the delivery needle 35 and preventing further distal displacement of the obturator 11. Thus, the obturator may provide additional support for the delivery needle and assist in piercing tissue, particularly for hard tumors. To reach liver tumors, the delivery needle 10 may extend distally 15 to 20 centimeters from the proximal port 15. The delivery needle 10 may have a jacket 17 of an insulating material such as parylene or Teflon® on its outer surface.

The biopsy needle 30 may be of either an aspirating or coring type as is well known in the art. Note that the biopsy needle 30 may have a proximal handle 45. When the biopsy needle is inserted into the proximal port 15 of the delivery needle 10, the proximal handle 45 abuts against the proximal port 15, preventing further distal displacement within the lumen 20. The biopsy needle 30 may have a blunt distal end 31 or a sharpened distal end 32. In addition, the biopsy needle 30 may further comprise a stylet 29 having a matched point 34 to aid in strengthening or stiffening the biopsy needle 30 and assist piercing tissue with the needle 30. The biopsy needle 30 is preferably 20 to 23 gauge and most preferably 20 to 21 gauge. The lumen of the biopsy needle 30 is preferably greater than 0.017" and most preferably at least 0.022". The biopsy needle 30 may be inserted into the lumen 20 of delivery needle 10 and both inserted into tissue as a unit such that the biopsy needle 30 acts as an obturator 11. Use of either a biopsy needle 30 or the obturator 11 in this way allows the delivery needle 10 to have a flat distal end, lessening trauma to internal organs from movements of the delivery needle 10 during exchange of the biopsy needle 30 and the ablation needle 35.

Figure 3A:
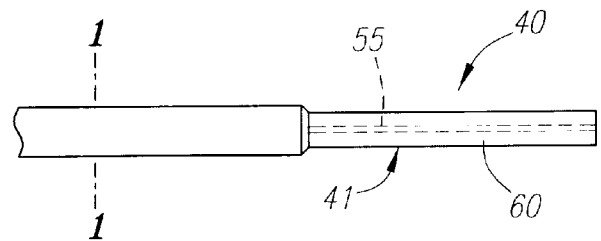
FIG. 3a is a side view of an open-tip monopole antenna according to one embodiment of the invention.
Figure 3B:
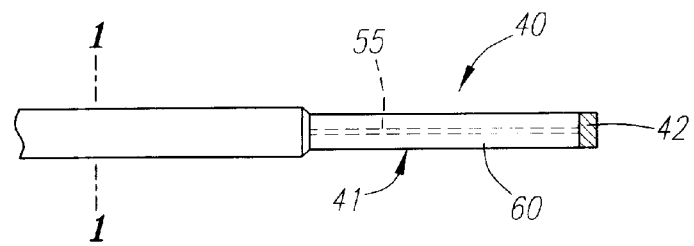
FIG. 3b is a side view of a dielectric or metal tip monopole antenna according to one embodiment of the invention.

Turning now to FIGS. 3a through 3e, the microwave antenna 40, formed by the distal projection of the ablation needle 35, may take any of several well-known forms in the art. For example, FIGS. 3a and 3b illustrate embodiments in which the microwave antenna comprises a monopole antenna 41 as described by Labonte et al., "Monopole Antennas for Microwave Catheter Ablation," *IEEE Trans. Microwave Theory Tech.*, vol. 44, no. 10, pp. 1832–1840, Oct. 1996, the contents of which are hereby incorporated by reference. In such embodiments, the distal projection of the ablation needle comprises the previously described center conductor 55 surrounded by the dielectric material 60. If, as illustrated in FIG. 3a, the center conductor 55 extends to the distal end of the distal projection, thereby contacting tissue when in use, the monopole antenna 41 is referred to as an open-tip monopole antenna. In other embodiments, a tip 42 prevents the center conductor 55 from directly contacting tissue as illustrated in FIG. 3b. If the tip 42 comprises a dielectric material, the monopole antenna 41 is referred to as a dielectric-tip monopole. If the tip 42 comprises a metallic material, the monopole antenna 41 is referred to as a metal-tip monopole.

Figure 3C:
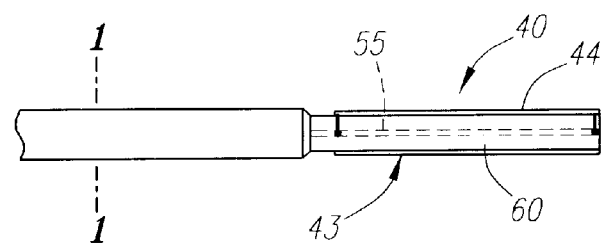
FIG. 3c is a side view of a dipole antenna according to one embodiment of the invention.
Figure 3D:
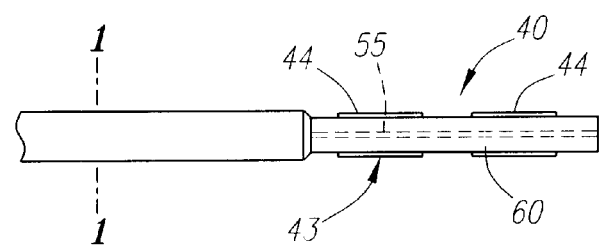
FIG. 3d is a side view of a dipole antenna according to one embodiment of the invention.
Figure 3E:
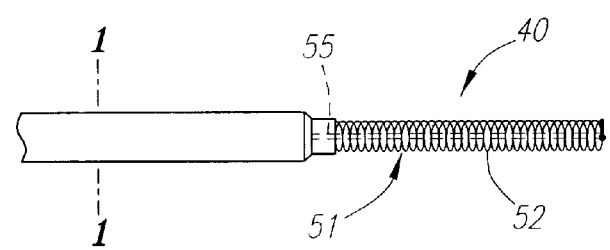
FIG. 3e is a side view of a helical coil antenna according to one embodiment of the invention.

Alternatively, the distal projection of the ablation needle 35 may form a dipole antenna 43 as illustrated in FIGS. 3c and 3d. In such embodiments, the distal projection of the ablation needle 35 comprises the center conductor 55 and surrounding dielectric material 60 as previously described. In addition, the distal projection of the ablation needle includes an outer conductor 44 forming one or more sections of coaxial transmission line in combination with the center conductor 55. This outer conductor 44 is electrically isolated from the delivery needle 10. It may be electrically coupled to the center conductor 55 as shown in FIG. 3c or may be electrically isolated from it as shown in FIG. 3d.

In yet another embodiment, the distal projection of the ablation needle 35 may form a helical coiled antenna 51. The helical coiled antenna 51 comprises the center conductor 55 and surrounding dielectric material 60 as previously described. In addition, the center conductor 55 has an extension that forms coils 52 about the dielectric material 60. The coils 52 are electrically isolated from the delivery needle 10. Stauffer et al., (1995) Interstitial Heating Tech. In: Seegenschmiedt et al. (eds.), *Thermoradiotherapy and Thermochemotherapy*, vol. 1, Springer, pp. 279–320 provide additional discussion of suitable dipole 43 and helical coil antennas 51, the contents of which is hereby incorporated by reference.

Turning now to FIGS. 13 through 15, an alternate embodiment of the present invention in which the ablation needle 35 and the delivery needle 10 do not couple together to create the coaxial transmission line is illustrated. The hollow delivery needle 10 possesses a proximal port 15 opening into a lumen 20 which extends through the delivery needle 10 to an open distal end as described previously. In addition, the delivery needle 10 preferably has a jacket of an insulating material such as parylene or Teflon® at least partially surrounding its outer surface (illustrated in FIG. 1a) or may be formed completely of a nonconductive material such as plastic. The delivery needle 10 is preferably 17 gauge, more preferably 18 gauge or higher. The ablation needle 35 is longer than the delivery needle 10 such that when the ablation needle 35 is inserted into the proximal port 15 and displaced until a stop 83 located on the ablation needle 35 engages the proximal port 15, a distal projection of the ablation needle 35 will extend from the distal end of the delivery needle 10. The distal projection of the ablation needle is adapted to form a microwave antenna 40. The ablation needle 35 includes a transmission line to couple to the microwave antenna 40. In the embodiment illustrated in FIG. 14, the transmission line in the ablation needle 35 comprises a coaxial transmission line 61. However, other types of transmission lines as known in the art may be used in ablation needle 35. To form the coaxial transmission line 61, the ablation needle 35 includes the center conductor 55 and surrounding dielectric material 60 as previously described. In addition, the ablation needle 35 includes an outer conductor 62 that circumferentially surrounds the dielectric material 60 to complete the coaxial transmission line 61. This outer conductor 62 extends distally from a coaxial connector 78 to the microwave antenna 40 and preferably comprises a highly conductive metal of a thickness of 1 to 10 times the skin depth (δ) as described herein. Outer conductor 62 preferably is protected by an outer coating of a material such as a fluoropolymer or parylene. Because ablation needle 35 includes the complete coaxial transmission line 61 and coaxial connector 78, the delivery needle 10 requires no electrical connector, and need merely end in the proximal port 15 through which the ablation needle 35 is inserted. The ablation needle 35 is distally displaced within the lumen 20 of the delivery needle 10 until the stop 83, here provided by the coaxial connector 78, prevents further distal displacement by contacting the proximal end of the delivery needle 10. In addition to acting as a stop 83, the coaxial connector 78 may be modified to connect to the proximal end of the delivery needle 10 through appropriate connectors (not illustrated). When the ablation needle 35 is displaced to contact the stop 83 with the proximal end of the delivery needle 10, the distal projection of the ablation needle 35 extends beyond the distal end of the delivery needle 10. This distal projection forms a microwave antenna 40. The microwave antenna 40 may be a monopole 41, dipole 43 or helical coil 51 as previously described and illustrated in FIGS. 3a through 3c. If center conductor 55 and outer conductor 62 are not comprised of a highly conductive metal, the center conductor 55 and the inner surface of the outer conductor 62 may be coated with a highly conductive metal to a thickness as previously described. To minimize trauma during insertion and ablation, the delivery needle 10 is preferably 17 gauge or higher, more preferably 18 gauge or higher.

As an alternative embodiment, instead of the coaxial connector 78, the delivery needle 10 may include a connector (not illustrated) comprising an outer portion of a coaxial connector and the ablation needle 35 may include a connector (not illustrated) comprising an inner portion of a coaxial connector. When the connectors are connected, the resulting coaxial connector is electrically coupled to the coaxial transmission line 61. In such an embodiment, the outer portion of the coaxial connector would have to electrically couple to the outer conductor 62 of the ablation needle 35.

It is to be noted that, regardless of the particular type of microwave antenna 40 implemented, the present invention provides advantages over prior art microwave antennas. In the present invention, the biopsy needle 30 and the delivery needle 10 may have already formed an insertion track before the microwave antenna 40 is inserted into an ablation site. Because the microwave antenna 40 may follow the existing insertion track, the microwave antenna 40 may possess a flat distal end. Prior art MCT microwave antennas typically had a sharpened distal end so that these antennas could be inserted into an ablation site. The SAR pattern of a microwave antenna 40 may be altered depending upon whether a flat or sharpened distal end is utilized. Thus, the present invention allows a clinician more control of the SAR patterns needed for a particular therapy.

Whether the ablation needle 35 and the delivery needle 10 are coupled to create the coaxial transmission line 50 or the ablation needle 35 includes the coaxial transmission line 61, the present invention will provide a variety of microwave antennas 40 which are inserted into a tumor through the lumen 20 of the delivery needle 10. The delivery needle 10 and the microwave antenna 40 together follow an insertion track in the body. The microwave antenna 40 may take a number of forms as previously described. Each of the forms, such as the monopole 41, has an effective antenna length which represents the longitudinal extent of tissue ablated by the microwave antenna 40 in the insertion track. The effective antenna length may depend upon the antenna design, the expected insertion depth, the expected amount of tissue perfusion, the expected duration and power of energy deliver, the frequency of the microwave power source, and additional factors. The effective antenna length may be greater, smaller or the same as the actual length of the physical components comprising the microwave antenna. Additionally, the field produced by the microwave antenna may be offset from the actual physical location of the antenna, either proximally or distally.

Track ablation is most efficiently performed only when the effective antenna length is accounted for during the procedure. Track ablation is necessary because tumors, such as liver tumors, can "seed" an insertion track as the microwave antenna 40 is withdrawn from the tumor. Therefore, it is beneficial to ablate the insertion track during withdrawal to kill any tumor cells displaced along the insertion track which would otherwise (potentially) act as "seeds" for future tumors. Moreover, track ablation helps to stem hemorrhage and bile leakage from the insertion track. After performing ablation of a tumor, the microwave antenna 40 may be withdrawn approximately an effective antenna length. Ablation would then be performed again, thus performing ablation in the insertion track without gaps and without excess overlap between successive ablations so as to kill displaced tumor cells while minimizing excess damage to the insertion track. Because only a small area surrounding the insertion track need be ablated, and to minimize damage to healthy tissue during track ablation, the clinician may decrease the diameter of the field of the antenna and/or lengthen the field to speed track ablation time. For example, a 48° C. isotherm may be desired 20 mm radially from the antenna during tumor ablation whereas the same 48° C. isotherm may be desired just 1 mm radially from the antenna during track ablation. These alterations to microwave field diameter and length may be made by decreasing the power or changing the frequency of the microwave power source. In addition or alternatively, the antenna field may be altered by changing the physical dimensions of the microwave antenna 40 by, for example, proximally or distally displacing the ablation needle 35 within the lumen 20 of the delivery needle 10. Alternatively, the ablation needle 35 used for tumor ablation could be withdrawn from the delivery needle 10 and replaced with an ablation needle 35 specialized for track ablation. This specialization would be such that the microwave antenna 40 would possess a field suitable for faster track ablation.

In a preferred embodiment of the present invention, a clinician may gauge whether the modular needle apparatus has been withdrawn a sufficient distance by observing a plurality of first markings 85 (illustrated in FIG. 2) distributed on the outside of the delivery needle 10. The plurality of first markings 85 are spaced apart a distance approximately equal to the effective antenna length. For example, if the effective antenna length were 20 millimeters, the delivery needle 10 would have markings 85 spaced apart approximately 18 to 20 millimeters. Thus, various models of the present invention having various effective antenna lengths would have first markings 85 spaced apart accordingly. If the delivery needle 10 has an electrically or thermally insulating jacket 17 of materials such as PE, PTFE or parylene, the first markings 85 may be printed on the jacket 17. After performing ablation of a tumor, the microwave antenna 40 may be withdrawn approximately an effective antenna length as gauged by observing first markings 85. Ablation would then be performed again, thus performing ablation in the insertion track without gaps and without excess overlap between successive ablations so as to kill displaced tumor cells while minimizing excess damage to the insertion track.

A clinician would observe first markings 85 differently according to the type of procedure being performed. For example, in a percutaneous procedure, the clinician would observe first markings 85 as the delivery needle is withdrawn from the skin of a patient. In a laparoscopic procedure, because a trocar may have been used to access a target organ, the modular needle apparatus may have been introduced through a cannula so that the clinician views the first markings 85 as the delivery needle 10 is withdrawn from the cannula. In an open surgical or laparoscopic procedure, the clinician may view the first markings 85 as the delivery needle 10 is withdrawn from the liver.

The plurality of first markings may be visible to the human eye or may be imaged using alternative means. For example, the plurality of first markings 85 may comprise a diamagnetic or paramagnetic material that gives an artifact observable with MRI. As one of ordinary skill in the art will appreciate, the remainder of the modular needle apparatus may be made of MRI-compatible materials for use during an MRI imaged procedure. Alternatively, the plurality of first markings 85 may comprise a radiopaque material visible during a fluoroscopic procedure. Finally, the plurality of first markings 85 may comprise a material having, e.g., a roughened surface visible to ultrasound imaging systems. It is to be noted that if the markings are imaged by means other than direct vision (e.g., a fluoroscopic procedure), the plurality of first markings may be located on the ablation needle rather than being located on the delivery needle.

A second marking 86 (also illustrated in FIG. 2) may be added on the outer surface of the delivery needle 10 (typically near the distal end) to indicate that the extent of the tissue ablated by the microwave antenna 40 has approached the surface of an organ containing the abnormality being ablated, for example, a tumor-containing liver. Thus, the second marking 86 will be located approximately at the proximal edge of effective antenna length, or field, of the microwave antenna 40. The second marking 86 would thus approximate the proximal edge of ablated tissue during a track ablation step. When the clinician observes the second marking 86, no more microwave energy would be delivered as the modular needle apparatus is further withdrawn from the patient. However, with the second marking 86 adjacent the edge of the liver, a final ablation of the insertion track may be performed. In an open laparoscopic or surgical procedure in which the clinician can observe delivery needle and the liver under direct vision, any second marking 86 visible to the eye would suffice. For procedures without such direct vision, a second marking 86 visible under the imaging system being used is needed. Alternatively, if the procedure is performed using MRI, a second marking 86 comprised of, for example, diamagnetic or paramagnetic material that gives an artifact observable with MRI is desirable. If the procedure is performed using ultrasound, a second marking 86 that is visible on ultrasound is preferable. Finally, if the procedure is performed using fluoroscopy, a radiopaque second marking 86 is desirable. Regardless of the type of procedure performed, to use the second marking 86, the position of the outer surface of the liver would need to be known by using the imaging systems used to observe the second marking 86 or by another imaging system either simultaneously or in sequence. Similarly to the plurality of first markings, the second marking 86 may be located on the ablation needle rather than on the delivery needle if the second marking is observed through an imaging system other than direct vision with the human eye.

It is to be noted that for the embodiments of the modular needle apparatus illustrated in FIGS. 13–15, the delivery needle 10 and the ablation needle 35 are not necessarily connected together during an ablation procedure. However, during a track ablation procedure wherein a clinician gauges the distance to partially withdraw the delivery needle 10 by observing the plurality of first markings 85 (illustrated in FIG. 2), the delivery needle 10 and ablation needle 35 may be connected together to assure that the ablation needle 35 is appropriately withdrawn as the delivery needle 10 is withdrawn. As one of ordinary skill in the art would appreciate, the connector(s) (not illustrated) necessary to connect the delivery needle 10 and the ablation needle 35 together may comprise many different embodiments. For example, an external clamp could attach about the proximal ends of the ablation needle 35 and the delivery needle 10, thereby effecting a connection. As discussed previously, the field of the microwave antenna may be adjusted to one more suitable for track ablation. Thus, the relative position of the ablation needle 35 and delivery needle 10 may be altered during track ablation as compared to tumor ablation. For example, if the delivery needle 10 functions to partially shield the microwave antenna during tumor ablation, the delivery needle 10 may be proximally displaced with respect to the ablation needle 35 during track ablation to further expose the microwave antenna, thereby effectively lengthening the field of the microwave antenna.

To assist coupling a microwave power source to the microwave antenna 40, the coaxial connector 75, 76 and 78 as used in the various embodiments described herein may comprise a standard coaxial connector such as an SMA connector. Alternatively, the coaxial connector may be a coaxial connector of a custom design for ease of assembly.

The present invention also includes a system for biopsy and ablation of tumors. The system comprises a modular needle apparatus in one of the various embodiments as described herein. An example system is illustrated in FIG. 2. This system includes the delivery needle 10 and ablation needle 35 of FIGS. 1a and 1c. Also included is an obturator 11, a biopsy needle 30 and a stylet 29 with a matched point 34 for the biopsy needle 30. A syringe 58 is shown for coupling to the biopsy needle 30 during aspiration of a tissue sample. As discussed herein, an assembly tool 56 aids the connection of the ablation needle 35 and the delivery needle 10. The system would further comprise a microwave power source 59 for coupling to the modular needle apparatus by connecting to the coaxial connector 75. The microwave power source will preferably generate microwave energy in the frequency range of 0.3 to 3.0 GHz. More preferably, the microwave antenna 40 and the microwave power source are adapted to operate at 0.915 or 2.45 GHz. The particular frequency or frequency range generated by the microwave power source will affect the SAR pattern of the microwave antenna 40. The clinician may thus adjust the microwave power source to generate a desired SAR pattern as required by a particular tumor.

Figure 4:
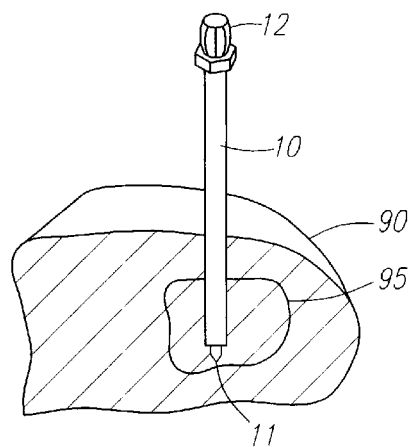
FIG. 4 is a side view illustrating the delivery needle with an obturator inserted into a tumor.
Figure 5:
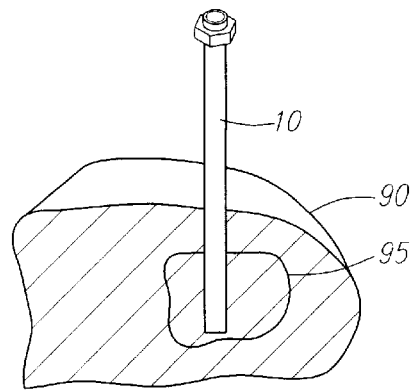
FIG. 5 is a side view of the delivery needle inserted into a tumor with the obturator withdrawn.
Figure 6:
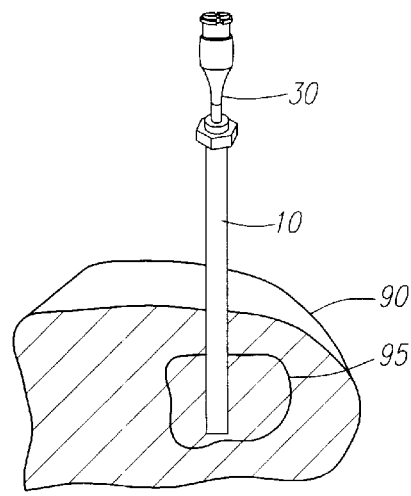
FIG. 6 is a side view of the biopsy needle inserted into the delivery needle.
Figure 7:
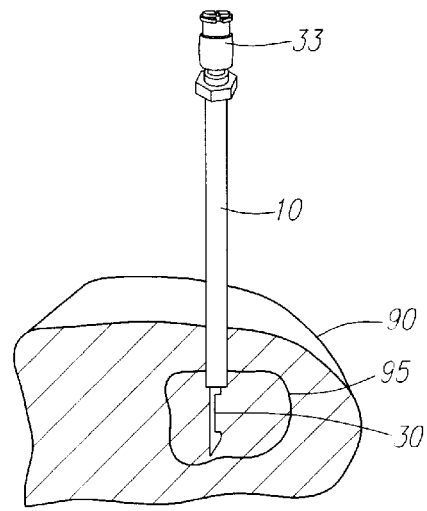
FIG. 7 is a side view of the delivery needle withdrawn slightly so as to expose the tip of the biopsy needle.

The present invention includes methods of biopsy and ablation using the disclosed modular needle apparatus. Turning now to FIGS. 4–12, a method of biopsy and ablation is illustrated using the modular needle apparatus as shown in FIGS. 1a–1c. As discussed herein, this embodiment creates the coaxial transmission line 50 after connecting together connector 65 on the ablation needle 35 to connector 70 on the delivery needle 10. As illustrated in FIG. 3, the delivery needle has an obturator 11 in the lumen 20 to stiffen the delivery needle 35 and assist piercing of tissue. Preferably, a percutaneous procedure is performed. If, however, a laparoscopic procedure is performed, the delivery needle 10 may be introduced through a trocar (not illustrated). Moreover, in an open surgical procedure, the delivery needle would enter tissue through an incision rather than entering percutaneously. The clinician may monitor the procedure with an imaging device such as MRI or ultrasound to guide the insertion of the delivery needle 10 into a patient until the delivery needle 10 is suitably positioned with respect to a tumor 95 located within the liver 90. Such a suitable position will depend upon the shape and position of the tumor 95 and the SAR pattern of the particular microwave antenna 40 used. Having inserted the delivery needle 10 properly with respect to the tumor 95, the clinician may withdraw the obturator 11 as illustrated in FIGS. 4 and 5. The clinician is now ready to perform a biopsy of the tumor 95 using a biopsy needle 30 inserted through the lumen 20 of the delivery needle 10. The clinician may perform this biopsy in a number of ways. For example, the biopsy needle 30 may be distally displaced within the lumen 20 until the distal end of the biopsy needle protrudes from the delivery needle 10 into the tumor 95. Alternatively, as illustrated in FIG. 6, the clinician may distally displace the biopsy needle within the lumen 20 until the distal end of the biopsy needle is proximally adjacent the distal end of the delivery needle 10. The clinician then exposes the distal end of the biopsy needle to the tumor 95 so that a tissue sample may be taken by proximally withdrawing the delivery needle 10 with respect to the biopsy needle 30 as illustrated in FIG. 7.

Figure 8:
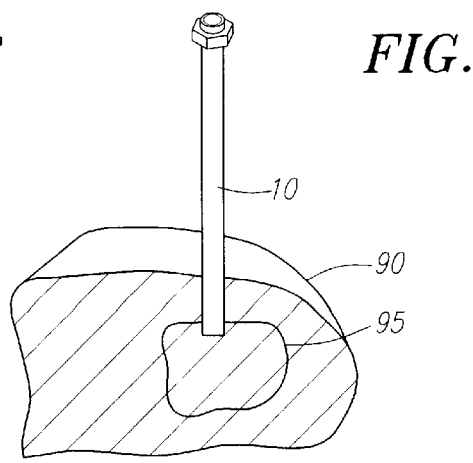
FIG. 8 is a side view of the delivery needle inserted into a tumor with the biopsy needle withdrawn.
Figure 9:
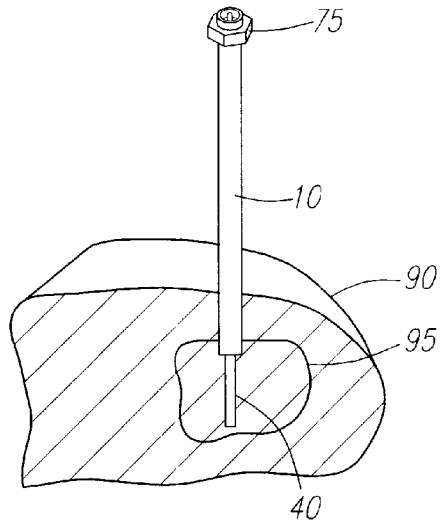
FIG. 9 is a side view of the ablation needle inserted into the delivery needle so as to form the microwave antenna.
Figure 10:
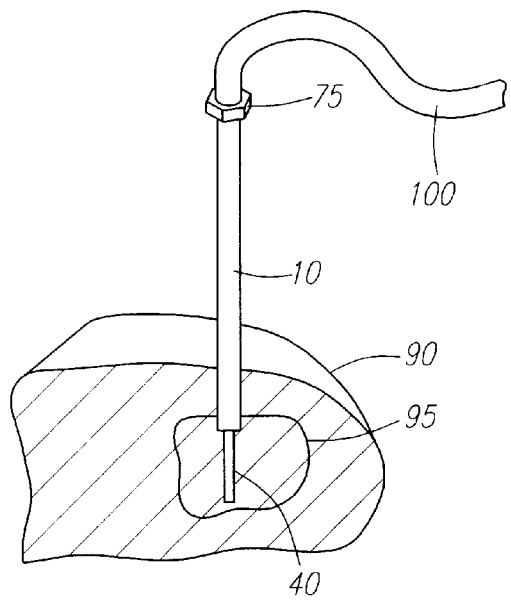
FIG. 10 is a side view of a flexible coaxial extension cable connected to the modular needle apparatus of FIG. 9.
Figure 11:
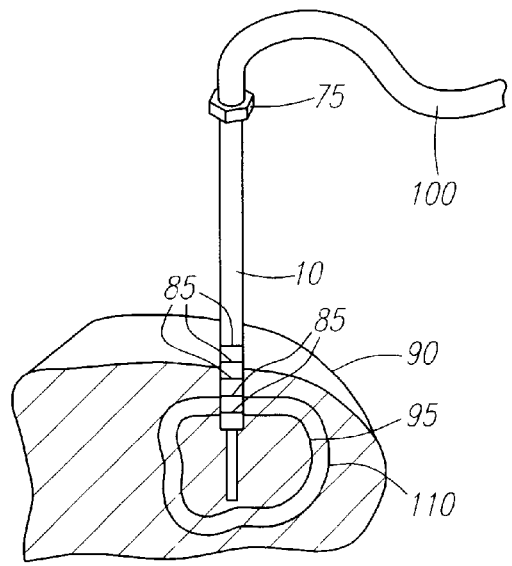
FIG. 11 is a side view of the microwave antenna ablating the tumor.
Figure 12:
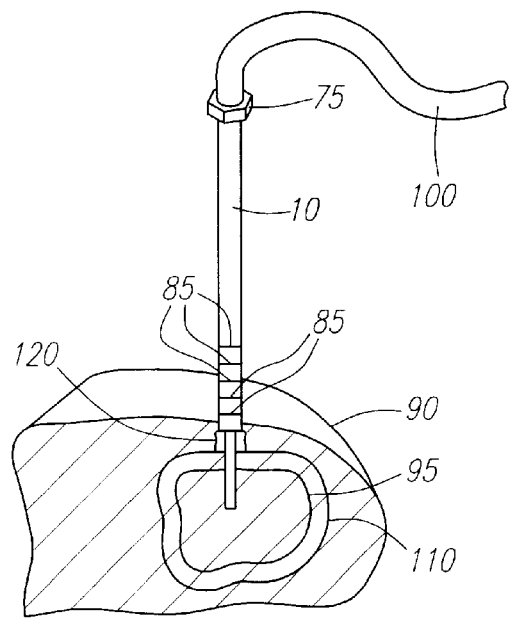
FIG. 12 is a side view of the microwave antenna ablating the insertion track.

As an alternative to the steps shown in FIGS. 4–7 as described thus far, biopsy needle 30 may be introduced with delivery needle 10 as a unit, and would appear as in FIG. 7. In that case, biopsy needle 30 preferably has a stiffening stylet 29 with a matched point 34 to aid in piercing tissue, particularly hardened tumors. To further aid in stiffening the biopsy needle 30, the biopsy needle 30 would preferably have a diameter very close to the inner diameter of delivery needle 10. The biopsy stylet 29 is then removed so that a biopsy can be taken. In either case, the biopsy needle 30 preferably comprises a luer-type fitting 33 on its proximal end. A syringe (illustrated in FIG. 2) is attached to fitting 33 and suction is applied to draw tissue into biopsy needle 30. After drawing a tissue sample into biopsy needle 30, the biopsy needle 30 is withdrawn from the lumen 20 of the delivery needle 10 as illustrated in FIG. 8. The clinician may optionally perform an additional biopsy, either at this point or following an ablation using the same or a different biopsy needle 30. Should the biopsy result indicate that the tumor 95 requires ablation, the clinician proceeds to insert the ablation needle 35 into the lumen 20 of the delivery needle 10. (Alternatively the clinician need not wait for the result). As described previously, the clinician distally displaces the ablation needle 35 within the lumen 20 until the second connector 65 on the ablation needle 35 is coupled to the first connector 70 on the delivery needle 10. In this fashion, a coaxial connector 75 is formed as illustrated in FIG. 9 so that microwave power source may be coupled through the coaxial transmission line 50 to the microwave antenna 40. Note that the insertion of the microwave antenna 40 into the tumor 95 does not require removal of the delivery needle 10. Thus, the clinician need not have to reinsert the delivery needle after a biopsy, avoiding the uncertainties of trying to align the delivery needle 10 with the previously formed insertion track. Furthermore, because the microwave antenna 40 follows the insertion track left by the biopsy needle 30, the microwave antenna 40 need not have a sharpened distal end. However, the present invention also contemplates methods wherein the clinician performs ablation before or in lieu of performing a biopsy or in a slightly different location than the biopsy site. In such an embodiment of the invention, the microwave antenna 40 would preferably have a sharpened distal end because the microwave antenna 40 will not be following a biopsy needle track. Turning now to FIG. 10, the clinician couples a microwave power source to the coaxial connector 75 through, e.g., a flexible coaxial cable 100. At this point the clinician may begin ablating the tumor 95. As illustrated in FIG. 11, the ablation continues until the area of ablated tissue 110 is larger than the tumor, thus insuring that the entire tumor 95 is destroyed. Finally, as illustrated in FIG. 12, the clinician may perform track ablation as previously described. By observing the plurality of first markings 85, the clinician partially withdraws the delivery needle 10 approximately an effective antenna length before performing another ablation. As described previously, a clinician would observe the first markings 85 differently according to the type of procedure being performed. For example, in a percutaneous procedure, the clinician would observe markings 85 as the delivery needle is withdrawn from the skin of a patient. In a laparoscopic procedure, the modular needle apparatus may have been introduced through a trocar so that the clinician views the markings 85 as the delivery needle 10 is withdrawn from the trocar. Finally, in an open surgical or laparoscopic procedure, the clinician may view the markings 85 as the delivery needle 10 is withdrawn from the liver 90. In this fashion, the insertion track 120 is ablated without gaps and with minimal overlap between ablations.

In embodiments of the invention wherein the maximum allowable withdrawal is gauged by observing the second marking 86 and stopping a withdrawal step when the second marking 86 is adjacent the surface of the liver 90 (indicating the proximal edge of the antenna pattern of the microwave antenna 40 is near the surface of the liver 90), the length over which the final ablation is performed may overlap the previously ablated track more so than the previous ablations. As described previously, the clinician will observe the second marking 86 differently depending upon the type of procedure being performed. If the procedure is an open surgical or laparoscopic one in which the surface of the liver 90 is directly visible, the clinician may view the second marking 86 directly. If the procedure is performed using MRI, the clinician may view the second marking 86 using MRI (provided that marking 86 is visible to MRI). Alternatively, if the procedure is performed using ultrasound or fluoroscopy, the second marking 86 will be viewed accordingly.

It is to be noted that, although the method of track ablation just described uses the modular needle apparatus of the present invention, the present invention contemplates a method of track ablation using prior art microwave ablation devices which include the plurality of first markings 85 and the second marking 86. Furthermore, the plurality of first markings 85 and second marking 86 and the method of using the same for track ablation may be applied to other interstitial thermotherapy procedures such as RF ablation, cryoablation or DC procedures. For example, on a cryoprobe, the plurality of first markings would be spaced apart the equivalent of the "effective antenna length" for the cryoprobe. This distance would correspond to the effective extent of ablated tissue produced by the cryoprobe during an ablation procedure.

Many widely differing embodiments of the present invention may be constructed without departing from the spirit and scope of the present invention. Therefore, it should be understood that the present invention is not to be limited to the particular forms or methods disclosed, but to the contrary, the present invention is to cover all modifications, equivalents and alternatives falling within the spirit and scope of the appended claims.

What is claimed is:

1. A modular needle kit for ablation through a puncture site, comprising:

a delivery needle insertable through the puncture site, said delivery needle having an open proximal end and an open distal end with a lumen extending therebetween;

an ablation needle adapted for ablating tissue abnormalities and coagulating an insertion track, said ablation needle comprising a transmission line and a microwave antenna electrically coupled to said transmission line, wherein said microwave antenna is insertable through said open proximal end of said delivery needle and extends beyond said distal end of said delivery needle when said ablation needle is distally displaced within said lumen of said delivery needle; and a positional connector adapted to detachably couple to said ablation needle in a fixed positional relationship with said delivery needle.

2. The kit of claim 1, wherein:

said delivery needle further comprises a first connector for electrically coupling to an outer conductor of said transmission line, said ablation needle further comprises a second connector electrically coupled to a center conductor of said transmission line, and said first and second connectors can be coupled to form a coaxial connector comprising said positional connector.

3. The kit of claim 1, wherein said positional connector comprises an external clamp attachable about the proximal ends of said ablation needle and said delivery needle.

4. The kit of claim 1, wherein said positional connector is adapted to detachably couple said ablation needle with said delivery needle in a fixed positional relationship for coagulation of an insertion track, wherein said fixed positional relationship is different from a positional relationship used for ablating tissue abnormalities.

5. The kit of claim 1, wherein said delivery needle comprises a distal portion having a diameter of 17 gauge smaller.

6. The kit of claim 1, further comprising a biopsy needle, said biopsy needle formed to be slidably disposed within said lumen of said delivery needle, wherein said biopsy needle extends beyond said distal end of said delivery needle when said biopsy needle is distally displaced within said lumen of said delivery needle.

7. The kit of claim 6, wherein said biopsy needle is adapted for use as an obturator of said delivery needle.

8. The kit of claim 6, wherein said biopsy needle is of an aspirating type or a coring type.

9. The kit of claim 1, wherein said delivery needle is formed of a nonconductive material.

10. The kit of claim 1, wherein said delivery needle is formed of plastic.

11. The kit of claim 1, wherein said delivery needle comprises a flat distal end.

12. The kit of claim 1, wherein said microwave antenna comprises a flat distal end.

13. A system for ablation of tissue comprising:

the kit of claim 1, and a microwave power source, wherein said transmission line is adapted to electrically couple to said microwave power source.

14. A method of ablating abnormalities in tissue, the method comprising the steps of:

providing the system of claim 13;

introducing the distal end of the delivery needle into tissue in a predetermined area;

inserting the distal end of the ablating needle into the lumen of the delivery needle through the open proximal end of the delivery needle;

advancing the distal end of the ablating needle to protrude from the distal end of the delivery needle; and ablating the tissue in the predetermined site by delivering microwave power to the microwave antenna through the transmission line.

15. The method of claim 14, wherein said introducing step comprises percutaneously introducing the distal end of the delivery needle into the tissue.

16. The method of claim 14, wherein said introducing step comprises laparoscopically introducing the distal end of the delivery needle into the tissue.

17. The method of claim 14, wherein said introducing step comprises introducing the distal end of the delivery needle into the tissue through an open surgical incision.

18. The method of claim 14, wherein said introducing step forms an insertion track, said method further comprising the steps of:

coupling said ablation needle in a fixed positional relationship with said delivery needle;

partially withdrawing the delivery needle and the ablation needle after said ablating step; and coagulating at least a portion of the insertion track.

19. The method of claim 14, further comprising the steps of:

providing a biopsy needle formed to be slidably disposable within the lumen of the delivery needle;

inserting the distal end of the biopsy needle into the lumen of the delivery needle through the open proximal end of the delivery needle before said step of inserting the distal end of the ablating needle into the lumen of the delivery needle;

sampling a tissue sample with the biopsy needle; and removing the biopsy needle from the delivery needle.

20. The method of claim 19, wherein said introducing step occurs while the biopsy needle is inserted through the lumen of the delivery needle.

21. A method of ablating an abnormality in tissue, the method comprising the steps of:

providing a system for ablation of tissue comprising:

a microwave antenna, a transmission line coupled to the microwave antenna, and a microwave power source, wherein the transmission line is adapted to electrically couple to the microwave power source;

introducing the distal end of the microwave antenna into tissue containing an abnormality to be ablated, whereby an insertion track is created proximal of the abnormality;

ablating the abnormality by applying microwave power to create a microwave field suitable for ablation of the abnormality in the tissue containing the abnormality;

altering the microwave field to produce a field suited for track coagulation; and coagulating at least a portion of the insertion track.

22. The method of claim 21, wherein said step of altering the microwave field comprises: decreasing the diameter of the microwave field, increasing the length of the microwave field, or both.

23. The method of claim 21, wherein said step of altering the microwave field comprises decreasing the microwave power applied.

24. The method of claim 21, wherein said step of alternating the microwave field comprises changing the frequency of the microwave power applied.

25. The method of claim 21, wherein said step of altering the microwave field comprises changing the physical dimensions of the microwave antenna.

26. The method of claim 25, wherein said introducing step comprises introducing the microwave antenna through a lumen of a delivery needle, and wherein the physical dimensions of the microwave antenna are changed by displacing the antenna within the lumen of the delivery needle.

27. The method of claim 26, wherein the antenna is displaced proximally with respect to the delivery needle.

28. The method of claim 26, wherein the antenna is displaced distally with respect to the delivery needle.

29. The method of claim 25, wherein the physical dimensions of the microwave antenna are changed by removing the microwave antenna and replacing it with a second microwave antenna of different physical dimensions.

30. The method of claim 21, wherein said step of ablating the abnormality comprises creating a predetermined isotherm at a first predetermined distance from the antenna, and wherein said step of coagulating the insertion track comprises creating the predetermined isotherm at a second predetermined distance from the antenna, wherein said second predetermined distance is less than said first predetermined distance.

31. The method of claim 21, wherein said step of coagulating the insertion track comprises:
coagulating a first portion of the insertion track;
repositioning the antenna; and
coagulating a second portion of the insertion track.

32. The method of claim 31, wherein the system for ablation comprises markings, and wherein said markings are used to determine the new position of the antenna during said repositioning step.

33. A method of ablating abnormalities in tissue, the method comprising the steps of:
introducing a delivery needle into a patient until the delivery needle is suitably positioned with respect to a tumor;
displacing a biopsy needle within a lumen of the delivery needle until a distal end of the biopsy needle protrudes from a distal end of the delivery needle;
performing a biopsy;
removing the biopsy needle from the delivery needle;
detachably positioning an ablation needle through the delivery needle into the tumor;
applying microwave power to the ablation needle to ablate the tumor;
removing the ablation needle from the tumor; and
removing the delivery needle from the patient.

34. The method of claim 33, wherein said introducing step comprises percutaneously introducing the distal end of the delivery needle into the patient.

35. The method of claim 33, wherein said introducing step comprises laparoscopically introducing the distal end of the delivery needle into the patient.

36. The method of claim 33, wherein said introducing step comprises introducing the distal end of the delivery needle into the patient through an open surgical incision.

37. The method of claim 33, wherein said displacing step occurs after said introducing step, such that the biopsy needle protrudes from the delivery needle into the tumor.

38. The method of claim 33, wherein said displacing step occurs before said introducing step, such that the biopsy needle acts as the obturator for the delivery needle, and such that the delivery needle and biopsy needle are introduced as a unit into the patient.

39. The method of claim 33, wherein said displacing step comprises displacing a coring-type biopsy needle within a lumen of the delivery needle.

40. The method of claim 33, wherein said displacing step comprises displacing an aspirating-type biopsy needle within the lumen of the delivery needle.

41. The method of claim 33, wherein said detachably positioning step comprises inserting an ablation needle having a sharpened distal end through the delivery needle into the tumor.

42. The method of claim 33, wherein said detachably positioning step comprises inserting an ablation needle having a flat distal end through the delivery needle into the tumor.

43. The method of claim 33, further comprising the step of mechanically coupling the ablation needle to the delivery needle.

44. The method of claim 43, wherein said mechanically coupling step comprises attaching an external clamp about the proximal end of the ablation needle and the proximal end of the delivery needle.

45. The method of claim 33, further comprising the steps of:
adjusting the relative position of the ablation needle and the delivery needle for track coagulation as compared to tumor ablation; and
coagulating the track.

46. The method of claim 45, further comprising the step of coagulating the track by steps.

47. The method of claim 33, further comprising the steps of:
performing a second biopsy through the delivery needle after said step of removing the ablating needle; and
removing the biopsy needle.

48. A method of ablating abnormalities in tissue, the method comprising the steps of:
introducing a delivery needle into a patient until the delivery needle is suitably positioned with respect to a tumor;
detachably positioning an ablation needle through a lumen of the delivery needle into or adjacent to the tumor;
applying microwave power to the ablation needle to ablate the tumor; and
removing the ablation needle from the patient while continuing to apply microwave power to the ablation needle.

49. The method of claim 48, further comprising the step of displacing a biopsy needle within a lumen of the delivery needle until a distal end of the biopsy needle protrudes from a distal end of the delivery needle prior to the step of detachably positioning.

50. The method of claim 49, further comprising the step of performing a biopsy.

51. The method of claim 50, further comprising the step of removing the biopsy needle from the delivery needle.

52. The method of claim 48, wherein said introducing step comprises percutaneously introducing the distal end of the delivery needle into the patient.

53. The method of claim 48, wherein said introducing step comprises introducing the distal end of the delivery needle into the patient through an open surgical incision.

54. The method of claim 48, wherein said detachably positioning step comprised inserting an ablation needle having a sharpened distal end through the delivery needle into the tumor.

55. The method of claim 48, wherein said detachably positioning step comprises inserting an ablation needle having a flat distal end through the delivery needle into the tumor.

56. The method of claim 48, wherein said removing step comprises removing the ablation needle and the delivery needle simultaneously while continuing to apply microwave power to the ablation needle.

57. The method of claim 48, wherein said removing step comprises removing the ablation needle in a stepped manner.

* * * * *